United States Patent [19]

Ohyama et al.

[11] Patent Number: 5,203,983
[45] Date of Patent: Apr. 20, 1993

[54] AIR-FUEL RATIO SENSOR FOR AN INTERNAL COMBUSTION ENGINE AND AN AIR-FUEL RATIO CONTROL APPARATUS USING THE SAME

[75] Inventors: Yoshishige Ohyama; Minoru Ohsuga, both of Katsuta, Japan

[73] Assignee: Hitachi, Ltd., Tokyo, Japan

[21] Appl. No.: 605,440

[22] Filed: Oct. 30, 1990

Related U.S. Application Data

[63] Continuation-in-part of Ser. No. 508,464, Apr. 13, 1990, which is a continuation of Ser. No. 251,878, Sep. 30, 1988.

[30] Foreign Application Priority Data

Oct. 5, 1987 [JP] Japan .................. 62-249827

[51] Int. Cl.⁵ ............................... G01N 27/26
[52] U.S. Cl. .................. 204/427; 204/424; 204/425; 204/428
[58] Field of Search .......... 204/424, 427, 428, 406; 123/489; 60/276; 338/34

[56] References Cited

U.S. PATENT DOCUMENTS

| | | | |
|---|---|---|---|
| 4,276,600 | 6/1981 | Hartford et al. | 123/489 |
| 4,664,773 | 5/1987 | Suzuki et al. | 204/406 |
| 4,891,122 | 1/1990 | Damno et al. | 204/427 |

Primary Examiner—John Niebling
Assistant Examiner—Bruce F. Bell
Attorney, Agent, or Firm—Antonelli, Terry, Stout & Kraus

[57] ABSTRACT

An air-fuel ratio sensor which includes a sensing portion made of a solid electrolyte exposed to exhaust gas from an internal combustion engine and a microprocessor for executing a predetermined processing on the basis of an output voltage of the sensing portion to identify an air-fuel ratio of fuel mixture supplied to the engine, in which a voltage deviation is obtained between the output voltage of the sensing portion and a reference voltage, which is provided for every temperature of the sensing portion and in accordance with a target air-fuel ratio preset in advance for an air-fuel ratio control, whereby the air-fuel ratio of the fuel mixture is identified on the basis of the thus obtained voltage deviation.

12 Claims, 5 Drawing Sheets

AIR-FUEL RATIO SENSOR FOR AN INTERNAL COMBUSTION ENGINE AND AN AIR-FUEL RATIO CONTROL APPARATUS USING THE SAME

CROSS-REFERENCES TO RELATED APPLICATIONS

This is a continuation-in-part of U.S. application Ser. No. 508,464, filed Apr. 13, 1990, which is a continuation of U.S. application Ser. No. 251,878, filed Sep. 30, 1988.

BACKGROUND OF THE INVENTION

1. Field of the Invention

The present invention relates to an air-fuel ratio sensor for an internal combustion engine, which is capable of detecting an air-fuel ratio of fuel mixture supplied to the engine both in the rich and lean regions as well as the stoichiometric air-fuel ratio, and more particularly to an improvement of an air-fuel ratio sensor of the type that an air-fuel ratio of the fuel mixture can be identified by simply amplifying a voltage produced by a sensing portion of the sensor. The present invention further relates to an air-fuel ratio control apparatus using the same.

2. Description of the Related Art

There has been known an air-fuel ratio sensor of the type that an air-fuel ratio of fuel mixture supplied to an internal combustion engine is detected directly from a voltage produced by a sensing portion made of solid electrolyte, oxide semiconductor and so on in response to the concentration of remaining oxygen included in exhaust gas from the engine over the wide range from the rich region to the lean one, including the stoichiometric air-fuel ratio (Japanese patent laid-open publication JP-A-62/67255 published Mar. 26, 1987).

According to the conventional technology as described above, there are provided means for detecting both a voltage induced by a sensing portion and an internal resistance thereof. The temperature dependence of the output voltage, which is accompanied by the sensing portion, is compensated by using the detected internal resistance thereof.

In the conventional sensor, however, there are problems in view of the accuracy and reliability of the measurement. Especially, the measurement accuracy of the sensor becomes worse in the lean and rich regions of an air-fuel ratio of fuel mixture, because the changing rate of a voltage induced by the sensing portion with respect to an air-fuel ratio is considerably small in those regions.

SUMMARY OF THE INVENTION

An object of the present invention is to provide an air-fuel ratio sensor for an internal combustion engine, which can detect an air-fuel ratio of fuel mixture supplied to the engine by simply amplifying a voltage produced by a sensing portion of the sensor in response to the concentration of remaining oxygen included in exhaust gas from the engine, with high accuracy and high reliability both in the rich region of the fuel mixture and the lean region thereof.

It is a further object of the present invention that a highly accurate and reliable air-fuel ratio control in an internal combustion engine is achieved by using the air-fuel ratio sensor as mentioned above. A feature of the present invention resides in an air-fuel ratio sensor for an internal combustion engine, which comprises a sensing portion, exposed to exhaust gas from the engine, for producing an output voltage in response to the concentration of remaining oxygen included in the exhaust gas, the sensing portion having an output characteristic of a step change portion changing stepwise near the stoichiometric air-fuel ratio and a portion changing linearly with respect to an air-fuel ratio on either side of the stoichiometric air-fuel ratio, and a microprocessor, which has a table of reference voltage versus temperature of the sensing portion and executes the following steps to sense an actual air-fuel ratio of the mixture: detecting a temperature of the sensing portion; determining a reference voltage retrieving the table in accordance with the detected temperature; and obtaining a signal indicative of the actual air-fuel ratio on the basis of a deviation between the reference voltage and the output voltage of the sensing portion.

Another feature of the present invention resides in an air-fuel ratio control apparatus for an internal combustion engine, using the air-fuel ratio sensor as mentioned above, in which the signal indicative of the actual air-fuel ratio is compared with a target air-fuel ratio preset for an air-fuel ratio control of fuel mixture supplied to the engine and a fuel control signal is produced in accordance with the comparison result.

According to the present invention, a reference voltage to be compared with an output voltage of a sensing portion is changed in accordance with a temperature of the sensing portion, whereby the temperature dependence of the output characteristic of the sensing portion can be removed and therefore a deviation between the reference voltage and the output voltage of the sensing portion depends only on an actual air-fuel ratio of an air-fuel mixture supplied to an engine.

As a result, a single, sufficiently large amplification factor can be used in order to amplify the deviation between the reference voltage and the output voltage of the sensing portion, whereby the changing range of the output voltage of the sensing portion with respect to the air-fuel ratio can be expanded and therefore the measurement accuracy of the sensor can be improved.

Further, since the reference voltage provided for comparison is selected at values respectively suited for the rich region and for the lean region in accordance with a target air-fuel ratio, which is set in advance for an air-fuel ration feed back control of an internal combustion engine, the measurement accuracy is improved in both regions, rich or lean, of the air-fuel ratio.

DESCRIPTION OF THE PREFERRED EMBODIMENTS

In the following, the explanation will be made of embodiments of the present invention with reference to the accompanying drawings.

Figure 1:
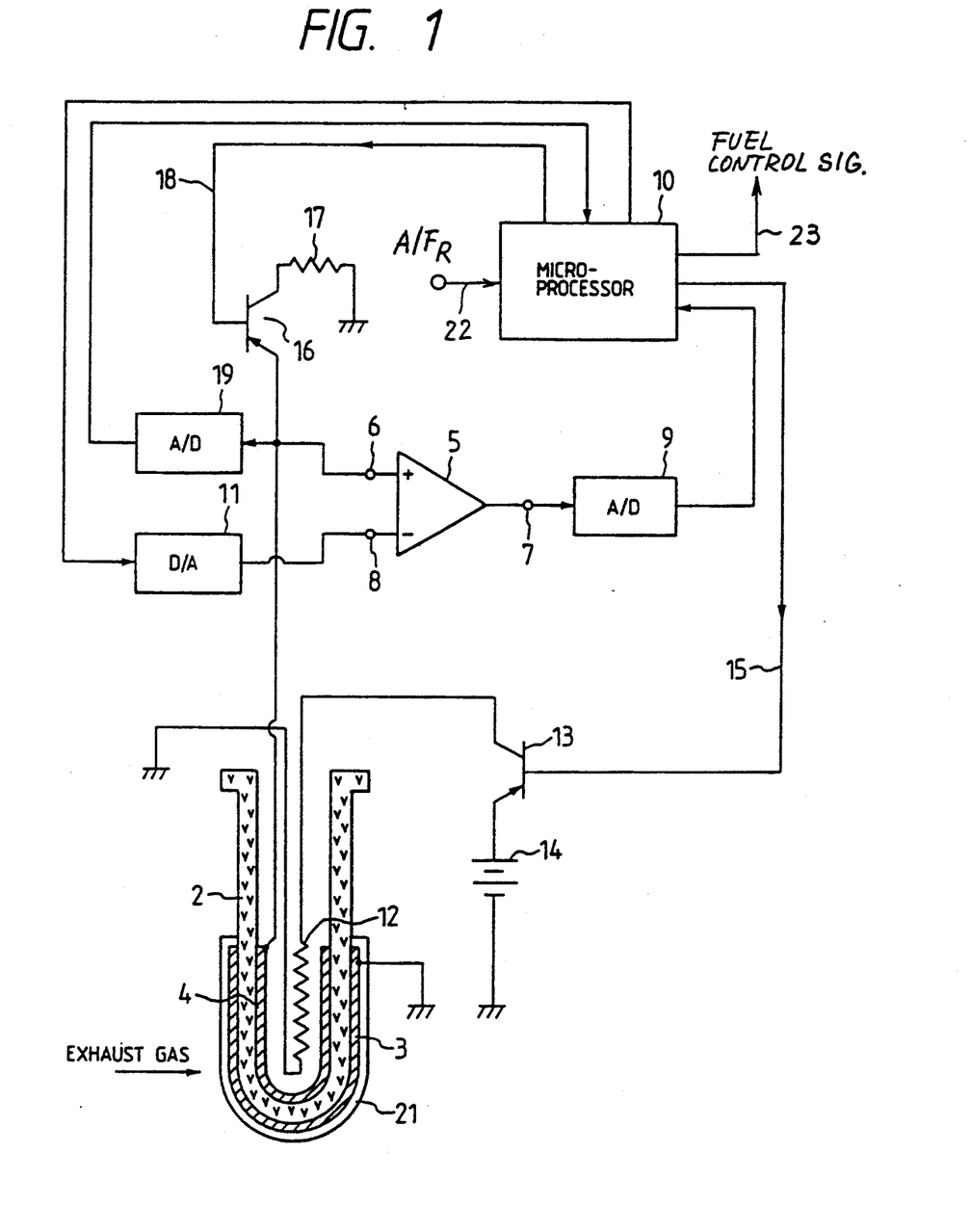
FIG. 1 schematically shows the overall configuration of an air-fuel ratio sensor according to an embodiment of the present invention.

In FIG. 1 there is shown the overall configuration of an air-fuel ratio sensor according to an embodiment of the present invention, in which solid electrolyte such as $Z_rO_2$, $Y_2O_3$ is employed as material of a sensing portion of the sensor. As shown in the FIG. 1, in a passage (not shown), through which exhaust gas from an internal combustion engine flows, there is provided solid electrolyte part 2, which is formed in a cylindrical form, one end of which is closed. An outer side of the cylindrical part 2 is exposed to the exhaust 1 gas, and air is introduced as a reference gas into the inside of the cylindrical part 2.

On both sides of the cylindrical electrolyte part 2, there are provided electrodes, i.e., electrode 3 on the outer side of the electrolyte part 2 and electrode 4 on the inner side thereof. The electrode 3 is brought into contact with the exhaust gas, which reaches thereat through porous protection layer 21, and the electrode 4 is in the atmosphere of air as the reference gas. The electrode 3 is grounded and the electrode 4 is coupled to a signal processing circuit described later. The solid electrolyte part 2, the two electrodes 3, 4 and the protection layer 21 constructs a sensing portion of the sensor.

There is provided heater 12 within the inside of the cylindrical solid electrolyte part 2. One end of the heater 12 is grounded and the other end thereof is coupled to a collector of transistor 13. An emitter of the transistor 13 is coupled to one end of DC power source 14, the other end of which is grounded. The transistor 13 is controlled by a signal given to its base through line 15, whereby the temperature of the sensing portion is maintained constant at a predetermined value so as to make the sensor operate in the desirable condition.

The electrode 4 is coupled to positive input terminal 6 of differential amplifier 5, which has a sufficiently large amplification factor determined according to the necessity. Thereby, an output voltage of the sensing portion, which appears across the electrodes 3 and 4 in response to the difference of the oxygen concentration between the exhaust gas and reference gas (air), is given to the amplifier 5. A reference voltage for comparison with the output voltage is applied to negative input terminal 8 of the amplifier through digital to analog (D/A) converter 11.

As a result, the amplifier 5 produces an amplified deviation signal in proportion to the deviation between the output voltage of the sensing portion and the reference voltage at its output terminal 7. The deviation signal is coupled to microprocessor 10 through analog to digital (A/D) converter 9.

The terminal 6 of the amplifier 5 is also coupled to an emitter of transistor 16, a collector of which is grounded through resistor 17. The transistor 16 is controlled by a signal given to its base from the microprocessor 10 through line 18. Further, analog to digital (A/D) converter 19 is coupled to the terminal 6, and the output of the converter 19 is given to the microprocessor 10.

Here, the following is to be noted. The microprocessor 10 is not always necessary to be a processor dedicated to the sensor. In the embodiment, it is shown as a microprocessor for executing various processings for an engine control. As input and output signals other than those relating to the operation of an air-fuel ratio sensor, there are shown only a target air-fuel ratio $A/F_R$ supplied through line 22 for an air-fuel ratio feedback control and a fuel control signal provided through line 23 to an actuator (not shown) of an fuel injector.

Further, the target air-fuel ratio $A/F_R$ is supplied externally in the figure, however it can also be prepared internally in the microprocessor 10 by a predetermined processing operation thereof. By way of example, as is well known, the microprocessor 10 receives various data indicative of the operational conditions of an engine from various sensors and executes a predetermined processing to thereby detect an output power required to be produced by the engine at that time. The target air-fuel ratio $A/F_R$ is determined on the basis of the thus obtained output power.

In such a processor, a processing operation for an air-fuel ratio sensor, which will be explained in detail later, can be built in the microprocessor 10 as one of tasks to be executed thereby. Naturally, the microprocessor 10 can be a sensor-born processor exclusively used for executing such processing operation for an air-fuel ratio sensor.

Figure 2:
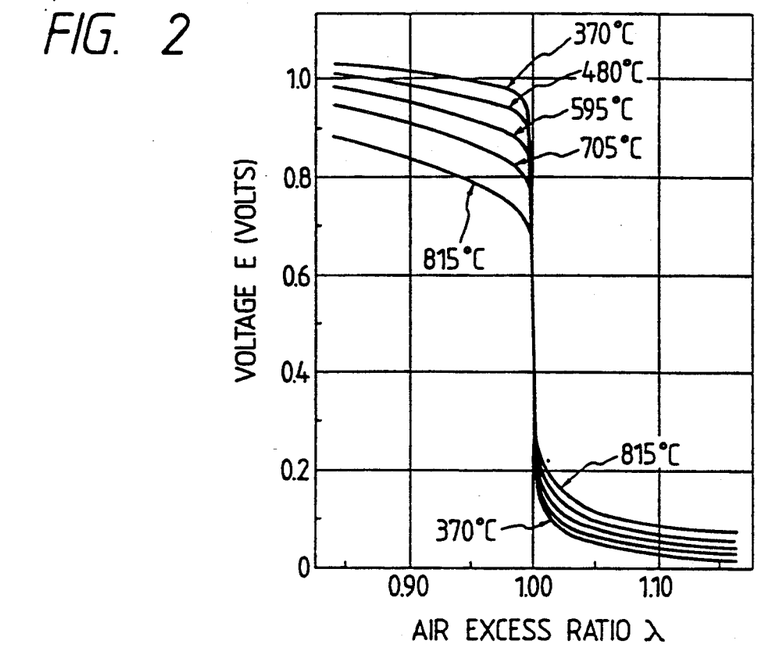
FIG. 2 is a graph for explaining the influence of the temperature of a sensing portion of an air-fuel ratio sensor on the output characteristics of the sensing portion with respect to air-fuel ratio represented in terms of air excess ratio.

In the air-fuel ratio sensor as described above, it is well known that the characteristics of the output voltage induced across the electrodes 3 and 4 with respect to air-fuel ratio represented in terms of air excess ratio is as shown in FIG. 2. Incidentally, in the following description, an air-fuel ratio will be represented by an air excess ratio $\lambda$, which is defined as a ratio of an air-fuel ratio to the stoichiometric value (14.7). Therefore, the stoichiometric air-fuel ratio is represented by $\lambda = 1.0$. In the rich region, in which an air-fuel ratio is smaller than 14.7, $\lambda$ becomes smaller than 1.0, whereas, in the lean region, in which an air-fuel ratio is larger than 14.7, it becomes larger than 1.0.

As shown in FIG. 2, the output voltage includes a step change portion which greatly changes stepwise at the stoichiometric air-fuel ratio ($\lambda = 1.0$). The output voltage changes very gently in the regions on both sides of the stoichiometric air-fuel ratio, i.e., in the rich region ($\lambda < 1.0$) and in the lean region ($\lambda > 1.0$). In addition, the output voltage in those regions widely varies in accordance with the temperature of the sensing portion.

When a sensing portion has the output characteristics as mentioned above, it is not practical to detect an air-fuel ratio over the wide range by simply amplifying the output voltage of the sensing portion, because the output voltage of the sensing portion widely varies. Usually, a reference voltage of a predetermined value, e.g., 0.5 volts, is set, and a deviation between the output voltage of the sensing portion and the reference voltage is obtained. The high accuracy detection of an air-fuel ratio is intended by amplifying the deviation with a sufficiently large amplification factor. With such a single, fixed reference voltage, however, the sufficiently large amplification factor can not be used, because the deviation between the output voltage and the reference voltage varies very widely in response to the temperature of the sensing port-ion.

Incidentally, the output characteristics of the sensing portion also varies in accordance with various combustible components, such as $C_3H_8$, CO, $H_2$, etc. usually included more or less in the exhaust gas. This affects measurement accuracy causing it to be worse. However, the influence of the combustible components can be removed by adjusting the temperature of the sensing portion to be maintained at a temperature higher than a predetermined value, desirably, above 600° C.

According to the present invention, it is possible to eliminate the aforesaid unfavorable influence of the temperature dependence of the sensing portion on the measurement accuracy and reliability, as follows. Before the detailed description of the operation of this embodiment, its principle will be explained, referring to FIG. 3.

Figure 3:
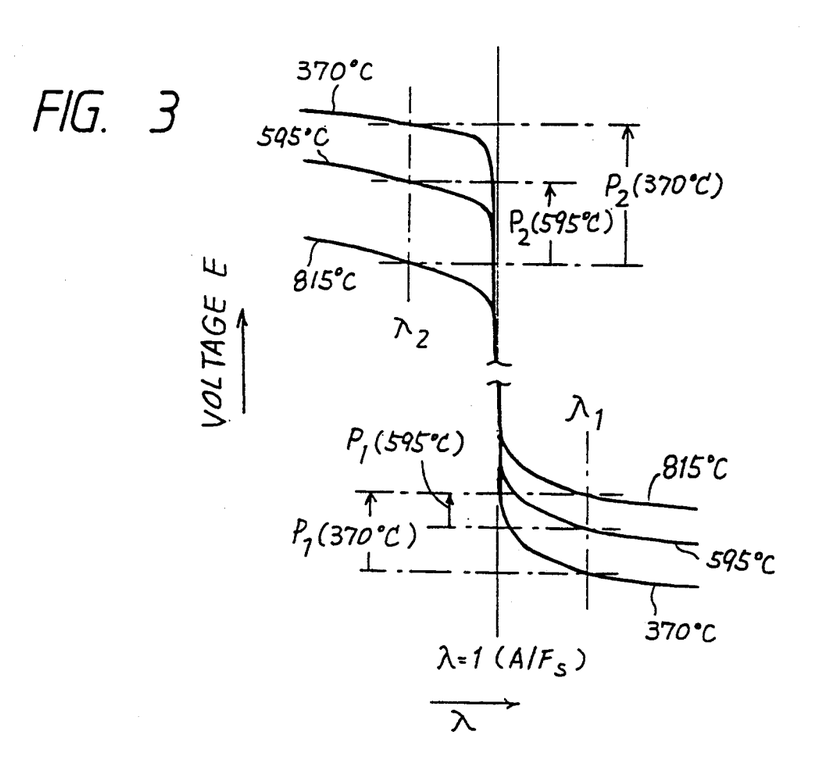
FIG. 3 is a drawing for explaining the operational principle underlying a processing operation executed by an air-fuel ratio sensor according to the present invention.

As examples for the following explanation, FIG. 3 shows only three characteristic curves of 815° C., 595° C. and 370° C. among the output characteristics as shown in FIG. 2. Further, for the convenience of the explanation, the characteristic curve of 815° C. is assumed as being standard, since the sensing portion is preferable to be operated at 600° C. or more, as already described. However, it will be understood from the following that any of the characteristic curves can be selected as standard.

Moreover, assuming that an air excess ratio is in the rich region and is equal to $\lambda_2$, and a temperature of the sensing portion is 595° C., there occurs a voltage difference $P_2$ (595° C.) in the output voltage E of the sensing portion, compared with the standard output voltage determined by the characteristic curve of 815° C.. There will occur the voltage difference $P_2$ (370° C.), if a temperature is 370. C. Similar observations can be made in the lean region.

In the case where a voltage difference for every temperature, such as $P_2$ (595° C.) or $P_2$ (370° C.), is known in advance, a standard output voltage of the sensing portion can be always known, if only a temperature is identified. Such a voltage difference will be called a reference voltage, below. The relationship of such a reference voltage with respect to temperature can be obtained experimentally and kept in a form of an appropriate table stored in a storage of the microprocessor 10.

If, therefore, only a temperature T of a sensing portion is detected, a corresponding voltage reference, i e., voltage difference $P_1(T)$ or $P_2(T)$, is determined by retrieving the table by the detected temperature T, and the standard output voltage can be obtained as a voltage deviation by subtracting the thus determined reference voltage $P_1(T)$ or $P_2(T)$ from the then existing output voltage E of the sensing portion.

After that, the air excess ratio can be identified by retrieving a table by the voltage deviation obtained as above, which table is an already known air-fuel ratio table or an air excess ratio table stored in the storage of the microprocessor 10 to hold the relationship of an air excess ratio and an output voltage of a sensing portion.

With this, the unfavorable influence of the temperature dependence of a sensing portion can be removed.

Further, since a single, standard output voltage of a sensing portion can be always obtained for a particular air excess ratio irrespective of temperature of the sensing portion, the output voltage of the sensing portion can be amplified by an amplifier with a single, sufficiently large amplification factor, whereby the changing range of the output voltage with respect to the air excess ratio can be expanded and the measurement accuracy is much improved.

In the following, the operation of the air-fuel ratio sensor shown in FIG. 1 will be explained, referring to FIG. 4, which is a flow chart illustrating the processing operation executed by the microprocessor 10 for the purpose of detection of an air-fuel ratio.

In the processing operation of this flow chart, the portion of steps 101 to 107 serves to detect the temperature of the sensing portion according to the following principle. In FIG. 1, assuming that the voltage at the terminal 6 upon turning-on of the transistor 16 is represented by U, the voltage thereat upon turning-off of the transistor 16 is represented by E, a resistance of the resistor 17 is represented by R, and an internal resistance of the electrolyte part 2 is represented by r, there exists the following relation:

$$U = \frac{R}{R + r} E \qquad (1)$$

The above formula (1) is rewritten as:

$$r = \left(\frac{E}{U} - 1\right)R \qquad (2)$$

Now, the explanation will be given to the processing operation illustrated by the flow chart of FIG. 4. This operation is repeatedly executed by the microprocessor 10 at intervals of 80 msec., for example. After start of the operation, an instruction is issued to the transistor 16 at step 101, whereby it is turned off. As a result, the resistor 17 is separated from the electrolyte part 2, and therefore, the voltage E appearing at the terminal 6 at that time means an electromotive force induced by the sensing portion in response to the oxygen concentration difference between the exhaust gas and the reference gas.

This voltage E is read into the microprocessor 10 at step 102 and stored in an appropriate storage therein at step 103. Then, the transistor 16 is turned on at step 104, whereby the resistor 17 is connected in series with the electrolyte part 2 and therefore the voltage appearing at the terminal 6 at that time becomes equal to the voltage U represented by the above formula (1). This voltage U is also read into the microprocessor 10 at step 105. Then, at step 106, the internal resistance r of the electrolyte part 2 is calculated on the basis of the voltages E and U in accordance with the formula (2).

As is well known, the internal resistance r of the electrolyte part 2 has the exponential relation to the temperature thereof. This relation is stored in advance in the storage of the microprocessor 10 in the form of a table T(r) of temperature T versus internal resistance r. Then, at step 107, the temperature T of the electrolyte part 2 is determined by retrieving the table with the internal resistance r obtained at step 106.

After the determination of the temperature T of the sensing portion, the processing operation goes to step 108, at which it is discriminated whether or not the detected temperature T is higher than 600° C. This reference temperature 600° C. is selected to avoid the influence of the combustible components included in the exhaust gas, which has been already described. In fact, it is known that if the temperature of the sensing portion is maintained above 600° C., the influential combustible components disappear in the exhaust gas or, at least, the influence thereof on the output characteristics of the sensing portion is reduced down as small as negligible.

If the temperature T of the sensing portion is judged to be lower than 600° C., the transistor 13 is turned on at step 110 to flow a current through the heater 12. Otherwise, the transistor 13 is turned off at step 109 to cut off the current flowing through the heater 12. After execution of either step 110 or 109, the operation goes to step 111.

As already mentioned, the operation of this flow chart is repeated at intervals of 80 msec. Therefore, step 108 and step 109 or 110 are also repeated at the same interval. This means that the current flowing through the heater 12 is intermittently controlled to maintain the temperature of the sensing portion at 600° C. Namely, these steps are provided for the purpose of temperature control of the sensing portion. If that purpose can be performed by any other measures, those steps are not necessary to be provided in the processing operation of this flow chart.

Next, at step 111, the transistor 16 is turned off again, and it is discriminated at step 112 whether or not target air-fuel $A/F_R$, which is set in advance as a target air-fuel ratio for the air-fuel ratio control of an internal combustion engine, is equal to the stoichiometric air-fuel ratio $A/F_S$. If both are equal to each other, the voltage appearing at the terminal 6 at that time is read as voltage E into the microprocessor 10 at step 113 and the processing operation ends. This voltage E is used for the air-fuel ratio control.

If the target air-fuel ratio A/F differs from the stoichiometric air-fuel ratio $A/F_S$, it is further discriminated at step 114 whether or not the former is larger than the latter. When the target air-fuel ratio $A/F_R$ is larger than the stoichiometric value $A/F_S$, i.e., in the case where the engine is instructed to operate with lean fuel mixture, a first voltage $P_1(T)$ is set at step 115 as the reference voltage $V_O$ for comparison with the output voltage of the sensing portion. On the contrary, if the target air-fuel ratio $A/F_R$ is smaller than the stoichiometric value $A/F_S$, i.e., in the case where the engine is to operate with rich fuel mixture, a second voltage $P_2(T)$ is selected at step 116 as the reference voltage $V_O$.

As will be understood from the graph of FIG. 2, it is desirable for the purpose of avoiding the influence of the temperature on the measurement accuracy that the voltage $P_1(T)$ or $P_2(T)$ is altered in response to the temperature T of the sensing portion, which was detected at step 107. Therefore, the microprocessor 10 has the relation of the first reference voltage $P_1(T)$ and the second reference voltage $P_2(T)$ with respect to temperature T in the form of a table stored in the storage thereof. At steps 115 and 116, $P_1(T)$ or $P_2(T)$ is determined as the reference voltage $V_O$ by retrieving the table with the temperature detected at step 107.

The thus determined reference voltage $V_O$ is output to the input terminal 8 of the amplifier 5 through the D/A converter 11 at step 117. On the other hand, the output voltage E of the sensing portion is applied to the input terminal 6 thereof, since the transistor 16 is turned off at step 111. Therefore, the differential amplifier 5 outputs the voltage in proportion to a deviation between the output-voltage E and the reference voltage $V_O$. At step 118, the voltage $V_1$, appearing at the output terminal 7 of the amplifier 5 in proportion to the deviation is read into the microprocessor 10.

At step 119, a table stored in the storage of the microprocessor 10 is retrieved with the voltage $V_1$, whereby the air-fuel ratio is determined. After that, the processing operation ends.

Figure 4:
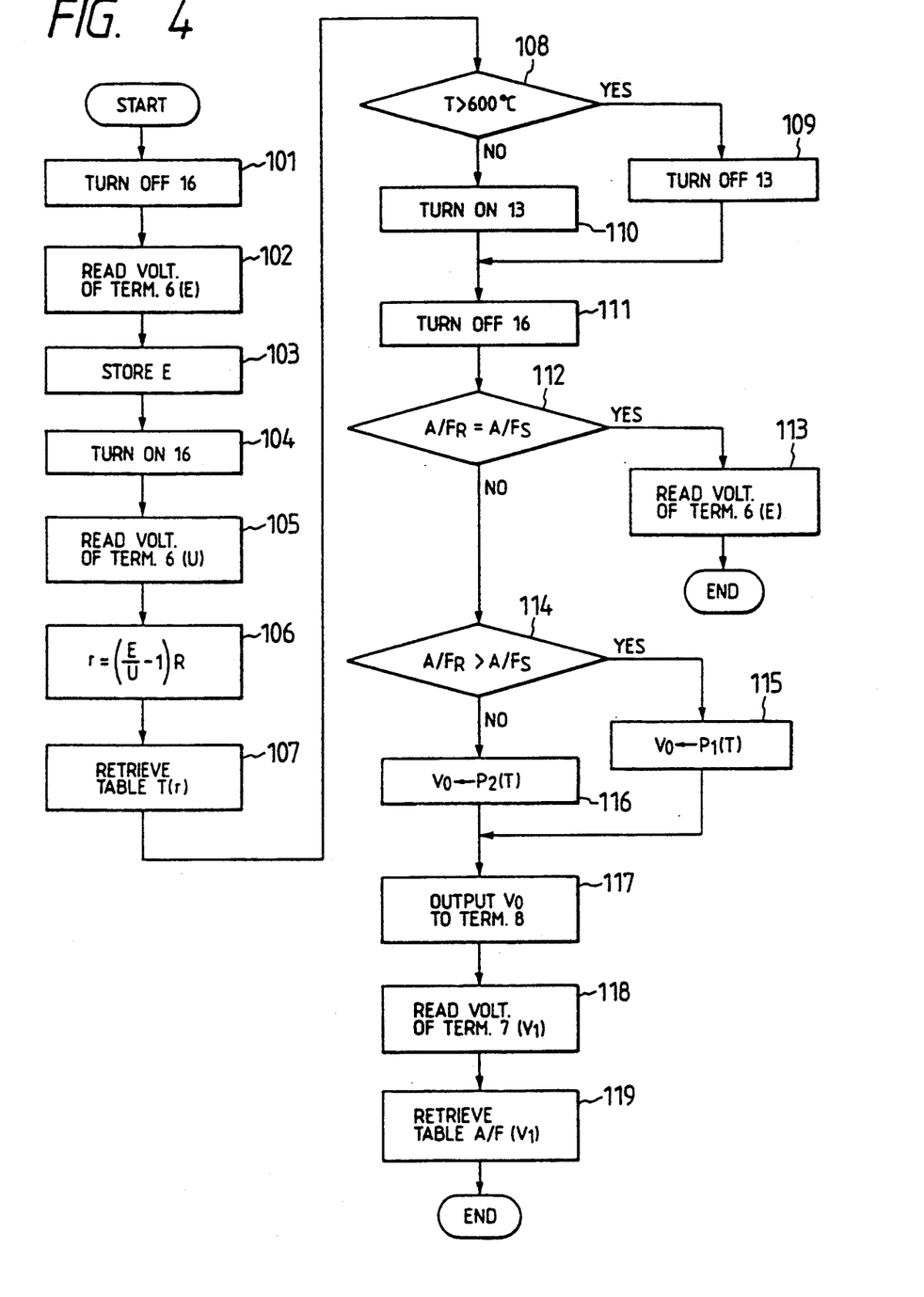
FIG. 4 is a flow chart illustrating the processing operation of a microprocessor of the air-fuel ratio sensor shown in FIG. 1.
Figure 5:
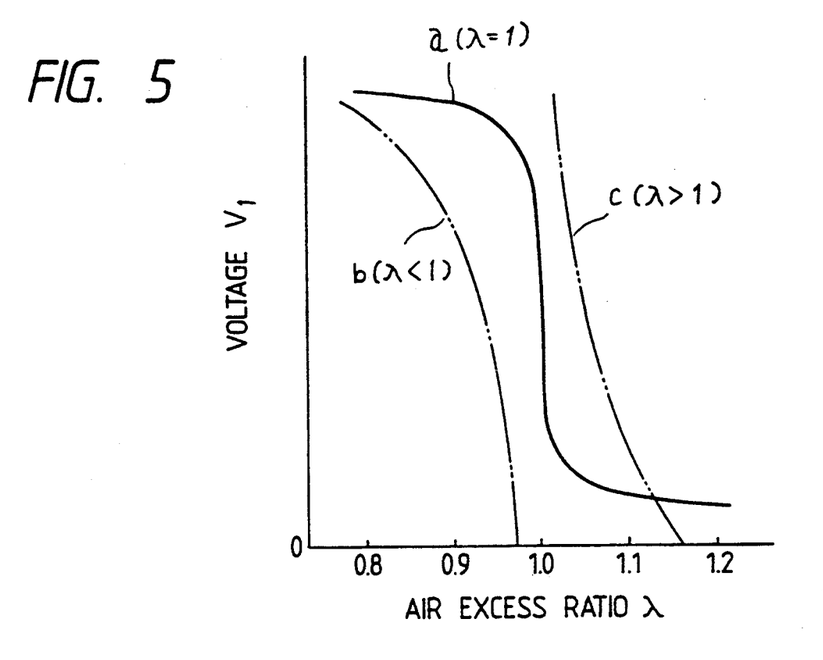
FIG. 5 is a graph showing the output characteristics of the sensor according to the embodiment of FIG. 1 with respect to air-fuel ratio represented in terms of air excess ratio.

An example of the output voltage $V_1$ of the amplifier 5 with respect to air excess ratio is shown in FIG. 5. When the target air-fuel ratio $A/F_R$ equals the stoichiometric value $A/F_S$ ($\lambda=1$), the voltage $V_1$ as shown by line a in FIG. 5 is taken into the microprocessor 10 through the converter 19 (cf. step 113 in FIG. 4).

Otherwise, the output voltage of the sensing portion is taken into the amplifier 5, wherein the deviation between the output voltage and the reference voltage is obtained and amplified by a large amplification factor thereof. As a result, the output voltage $V_1$ of the amplifier 5 becomes as shown by line b in FIG. 5, when $A/F_R$ is smaller than $A/F_S(\lambda<1)$, and as shown by line c, when $A/F_R$ is larger than $A/F_S(\lambda>1)$. Namely, the very moderate change of the output voltage of the sensing portion in the rich and lean regions is expanded as shown by lines b and c.

In the cases of $\lambda<1$ and $\lambda>1$, the table is retrieved in the microprocessor 10 on the basis of this voltage $V_1$ of the amplifier 5 (cf. step 119 in FIG. 4), whereby an air-fuel ratio of the mixture is identified. Since the output voltage $V_1$ of the amplifier 5 widely varies in the rich and lean regions, compared with the simple output voltage E of the sensing portion, as shown by line a, an actual air-fuel ratio of can be sensed with higher accuracy.

Figure 6:
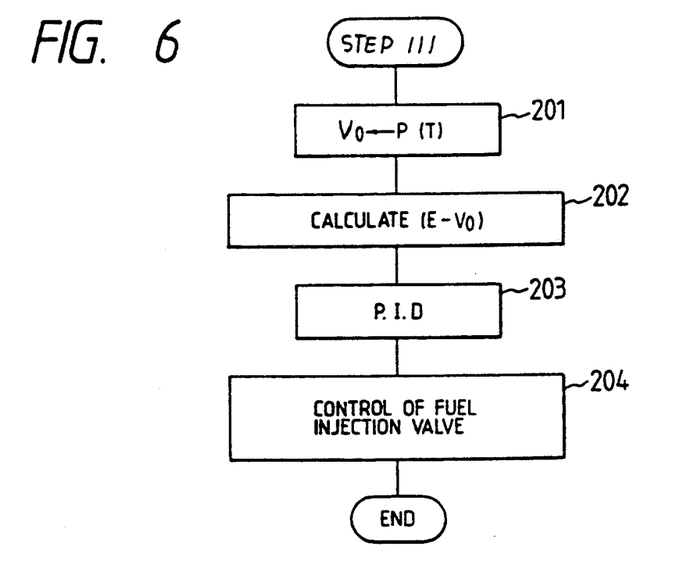
FIG. 6 is a flow chart illustrating a part of the processing operation of the microprocessor for the air-fuel ratio control, which is one of typical applications of the air-fuel ratio sensor of FIG. 1.

If a control apparatus for an internal combustion engine is designed to control the air-fuel ratio of fuel mixture supplied to the engine by a closed control loop, the value itself of the air-fuel ratio is not always necessary to be identified. FIG. 6 shows a flow chart of a processing operation in such a case, which is to be substituted for a part of the processing operation of the flow chart of FIG. 4, i.e., step 112 and the following.

In this case, at first, steps 101 to 111 in the flow chart of FIG. 4 are executed to obtain the temperature T of a sensing portion. After that, the processing of this flow chart is executed. Further, in this example, a deviation between an output voltage of the sensing portion and a reference voltage is obtained within the microprocessor 10 and by means of the processing operation thereof. In contradistinction thereto, such a deviation was obtained by the differential amplifier 5 in the example already described with reference to FIGS. 1 and 4. In this example, therefore, the differential amplifier 5 and the converters 9 and 19 as shown in FIG. 1 can be omitted.

After the temperature T is detected, a reference voltage $V_O$ is determined at step 201 accordingly. The microprocessor 10 has a table of voltage P(T) versus temperature T. The flow chart of FIG. 6 is not provided with two separate reference voltages as $P_1(T)$ and $P_2(T)$ in FIG. 4, but with only one reference voltage P(T). However, it can of course be provided with two separate reference voltages for every region of lean or rich. At this step 201, such a table is retrieved by the detected temperature T and the reference voltage $V_O$ is determined on the basis of the retrieved P(T).

Then, at step 202, the output voltage E of the sensing portion is compared with the reference voltage $V_O$, and the deviation (E-$V_O$) therebetween is calculated. At step 203, the deviation (E-$V_O$) is subjected to the processing of the proportional integral and differential (P-I-D) operation. As is well known, in this step 203, the air-fuel ratio feedback control is carried out. Namely, the deviation (E-$V_O$) is compared with a target air-fuel ratio A/$F_R$ to determine a control deviation. With existence of this step, the closed loop, air-fuel ratio feedback control is constituted. This control deviation is subjected to the aforesaid P-I-D processing to produce a fuel control signal.

The thus produced fuel control signal at step 203 is supplied to an actuator of a fuel injection valve at step 204, whereby the fuel injection valve controls the amount of injected fuel so as to make an actual air-fuel ratio of fuel mixture supplied to an engine follow the target air-fuel ratio A/$F_R$. After completion of step 204, the processing operation returns to step 101 of the flow chart of FIG. 4, and the operation as mentioned above is repeated in predetermined intervals.

Figure 7A:
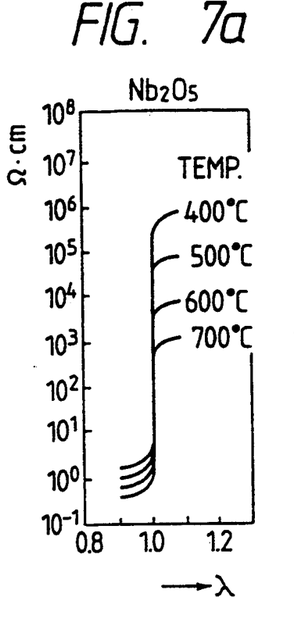
FIGS. 7a to 7c are graphs showing examples of the temperature dependence of change in the resistivity of oxide semiconductors, which can be employed as material for a sensing portion of an air-fuel ratio sensor of the present invention.
Figure 7B:
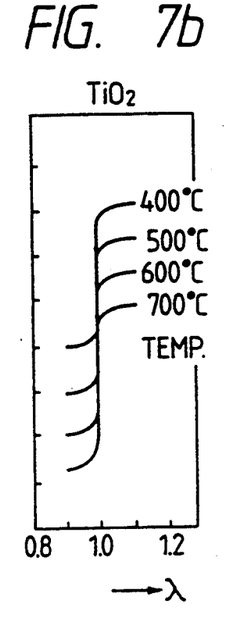
Figure 7C:
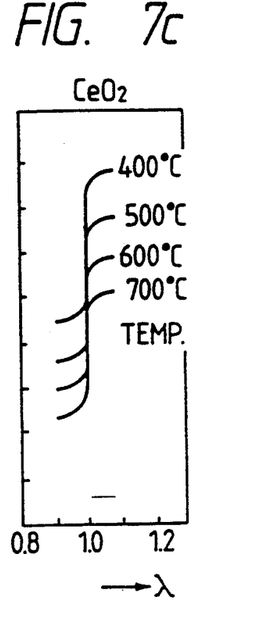

As already described, oxide semiconductor can be employed as material of a sensing portion. In this case, there is used the characteristics that the resistivity of the oxide semiconductor changes in response to the concentration of remaining oxygen included in exhaust gas from an internal combustion engine, i.e., the air-fuel ratio of fuel mixture supplied to the engine. In Figs. 7a to 7c, there are shown examples of the resistivity characteristics of $Nb_2O_5$, $TiO_2$, and $CeO_2$ with respect to air-fuel ratio represented in terms of air excess ratio.

As apparent from those figures, the resistivity characteristics widely changes sharply at the stoichiometric air-fuel ratio and has the temperature dependence, quite similarly to that of solid electrolyte as already mentioned. Accordingly, the present invention can be applicable to an air-fuel ratio sensor using such oxide semiconductor as material of a sensing portion. In the following, the explanation will be made of another embodiment of the present invention, in which oxide semiconductor is used.

Figure 8:
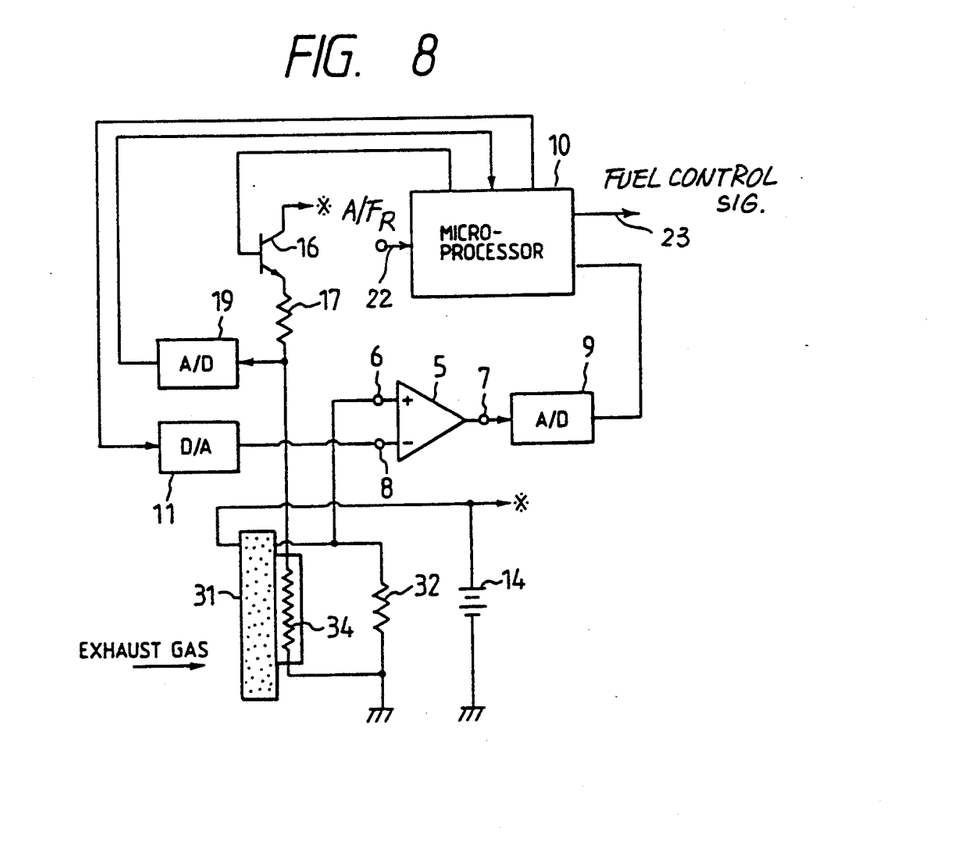
FIG. 8 schematically shows the overall configuration of an air-fuel ratio sensor according to another embodiment of the present invention.

FIG. 8 schematically shows the overall configuration of an air-fuel ratio sensor using oxide semiconductor. In the figure, the same reference numerals represent the same parts as in FIG. 1.

As shown in FIG. 8, oxide semiconductor part 31 functioning as a sensing portion is positioned at such a location that it can be in contact with the exhaust gas. A first electrode (not shown) provided on one side of the sensing portion is coupled to one of the DC power source 14. A second electrode (not shown) provided on the other side of the sensing portion is grounded through resistor 32. The resistor 32 functions to convert the change in the resistivity of the sensing portion in response to the concentration of the remaining oxygen into a voltage. This voltage corresponds to the output voltage of the sensing portion in FIG. 1. The second electrode is also coupled to the positive input terminal 6 of the differential amplifier 5, whereby the voltage appearing across the resistor 32 is applied to the amplifier 5 as one of two input signals.

Heater 34 made of platinum is provided neighbouring on or in contact with the sensing portion. Further, although it is of course that appropriate protecting measures are provided, they are omitted here in the figure. One end of the heater 34 is grounded and the other end thereof is coupled to the resistor 17. The resistor 17 is in turn coupled to the DC power source 14 through the transistor 16, which is controlled by a signal from the microprocessor 10. The other end of the heater 34 is also coupled to the microprocessor 10 through the A/D converter 19.

The negative input terminal 8 of the amplifier 5 is supplied with a reference voltage from the microprocessor 10 through the D/A converter 11, and an output voltage of the amplifier 5 appearing at the output terminal 7 is given to the microprocessor 10 through the A/D converter 9.

Assuming that a resistance of the platinum heater 34 is represented by $R_H$, that of the resistor 17 by R, and the voltage of the DC power source 14 by $V_d$, the voltage v appearing at a connecting point of the resistor 17 and the heater 34 is represented by the following formula:

$$v = \frac{R}{R_H + R} V_d \qquad (3)$$

The above formula is rewritten as:

$$R_H = \left( \frac{V_d}{v} - 1 \right) R \qquad (4)$$

As apparent from the formula (4), the resistance $R_H$ of the platinum heater 34 can be obtained from the voltage v. This means that the temperature T of the platinum heater 34, and hence the temperature of the sensing portion, can be obtained, because there is a known relation between the resistance $R_H$ and the temperature T of the platinum heater 34. With the thus determined temperature T of the sensing portion, the voltage $V_O$ to be applied to the terminal 8 of the amplifier 5 can be determined in the microprocessor 10. Therefore, the temperature of the sensing portion of this embodiment can be obtained in an analogous manner to the pertinent portion of the processing operation of the flow chart of FIG. 4.

Namely, after start of the processing operation, the transistor 16 is at once turned on, and then the voltage appearing at the connecting point of the resistor 17 and the heater 34 is read into the microprocessor 10 through the A/D converter 19. In the microprocessor 10, the resistance $R_H$ is calculated on the basis of the voltages v and Vd in accordance with the formula (4), and a predetermined table of temperature T versus resistance $R_H$ is retrieved with the calculated resistance $R_H$, whereby the temperature T is obtained.

The processing operation after that in this embodiment is the same as the corresponding portion, i.e., step 108 et seqq., in the processing operation of the flow chart of FIG. 4.

As described above, according to the present invention, the changing range of the output voltage of an air-fuel ratio sensor with respect to air-fuel ratio can be made remarkably wide both in the rich region and the lean region, which makes it possible to measure the air-fuel ratio with high accuracy. With such an air-fuel ratio sensor, the performance of an internal combustion engine can be improved without requiring the very large cost.

We claim:

1. An air-fuel ratio sensor for sensing an air-fuel ratio of air-fuel mixture supplied to an internal combustion engine, said air-fuel ratio sensor comprising:
   a sensing portion, exposed to exhaust gas from the engine, for producing an output voltage in response to the concentration of remaining oxygen included in the exhaust gas, said sensing portion having a temperature dependent output characteristic of a step change portion changing stepwise in the vicinity of stoichiometric air-fuel ratio of a mixture and a portion changing linearly with respect to an air-fuel ratio of a mixture on either side of said stoichiometric air-fuel ratio;
   a differential amplifier having two input terminals, one of which being provided with an output voltage of said sensing portion and the other input terminal being provided with a reference voltage, said differential amplifier produces an output signal indicative of a deviation between said output voltage and said reference voltage, said reference voltage being related to a temperature of said sensing portion; and
   a microprocessor circuit, which has stored therein a table of reference voltage versus temperature of said sensing portion, for detecting a temperature of said sensing portion, determining said reference voltage by retrieving said table on the basis of said detected temperature, inputting said output signal of said differential amplifier, and identifying an actual air-fuel ratio on the basis of said output signal.

2. An air-fuel ratio sensor for sensing an air-fuel ratio of air-fuel mixture supplied to an internal combustion engine, said air-fuel ratio sensor comprising:
   a sensing portion, exposed to exhaust gas from the engine, for producing an output voltage in response to the concentration of remaining oxygen included in the exhaust gas, said sensing portion having a temperature dependent output characteristic of a step change portion changing stepwise in the vicinity of stoichiometric air-fuel ratio of a mixture and a portion changing linearly with respect to an air-fuel ratio of a mixture on either side of said stoichiometric air-fuel ratio; and
   a microprocessor circuit, which has stored therein a table of reference voltage versus temperature of said sensing portion, for detecting a temperature of said sensing portion, determining a reference voltage by retrieving said table on the basis of said detected temperature, obtaining a voltage deviation between said output voltage of said sensing portion and said reference voltage, and identifying an actual air-fuel ratio on the said of said voltage deviation.

3. An air-fuel ratio sensor according to claim 3, wherein said microprocessor circuit in performing said detecting function detects an internal resistance of the solid electrolyte part, and identifies said temperature of said sensing portion on the basis of said detected internal resistance.

4. An air-fuel ratio sensor according to claim 3, wherein the detecting step comprises the following steps:
   step of detecting an internal resistance of the solid electrolyte part; and
   step of identifying the temperature of said sensing portion on the basis of the detected internal resistance.

5. An air fuel ratio sensor according to claim 1 or 2, wherein
   said sensing portion is composed of an oxide semiconductor part, which changes resistivity thereof in response to the concentration of remaining oxygen included in the exhaust gas, and means for converting the change of resistivity into a voltage as said output voltage of said sensing portion.

6. An air-fuel ratio sensor according to claim 5, further comprising:
   means for heating the oxide semiconductor part to maintain the temperature thereof at a predetermined value,
   wherein said microprocessor circuit in performing said detecting function detects a resistance of said heating means, and identifies said temperature of said sensing portion on the basis of said detected resistance.

7. An air-fuel ratio sensor according to claim 1, wherein said microprocessor circuit performs said determining, inputting and identifying functions when said detected temperature exceeds a predetermined value.

8. An air-fuel ratio sensor according to claim 2, wherein said microprocessor circuit performs said determining, obtaining and identifying functions when said detected temperature exceeds a predetermined value.

9. An air-fuel ratio sensor according to claim 1 or 2, wherein said microprocessor circuit in performing said determining function discriminates which is larger between said stoichiometric air-fuel ratio and a target air-fuel ratio provided for an air-fuel ratio feedback control of the fuel mixture, and sets a different reference voltage in response to the result of said discrimination.

10. An air-fuel ratio control apparatus for an internal combustion engine, comprising:
    a sensing portion, exposed to exhaust gas from the engine, for producing an output voltage in response to the concentration of remaining oxygen included in the exhaust gas, said sensing portion having a temperature dependent output characteristic of a step change portion changing stepwise in the vicinity of stoichiometric air-fuel ratio of a mixture and a portion changing linearly with respect to an air-fuel ratio of a mixture on either side of said stoichiometric air-fuel ratio;
    a differential amplifier having two input terminals, one of which being provided with an output voltage of said sensing portion and the other input terminal being provided with a reference voltage, said differential amplifier produces an output signal indicative of a deviation between said output voltage being related to a temperature of said sensing portion; and
    microprocessor circuit, which has stored therein a table of reference voltage versus temperature of said sensing portion, for detecting a temperature of said sensing portion, determining said reference voltage by retrieving said table on the basis of said detected temperature, inputting said output signal of said differential amplifier, comparing said output signal with a target air-fuel ratio preset for an air-fuel ratio control of the fuel mixture and outputting as a result of said comparison a control deviation and producing a fuel control signal in accordance with said control deviation.

11. An air-fuel ratio control apparatus for an internal combustion engine, comprising:

a sensing portion, exposed to exhaust gas from the engine, for producing an output voltage in response to the concentration of remaining oxygen included in the exhaust gas, said sensing portion having a temperature dependent output characteristic of a step change portion changing stepwise in the vicinity of stoichiometric air-fuel ratio of a mixture and a portion changing linearly with respect to an air-fuel ratio of a mixture on either side of said stoichiometric air-fuel ratio; and a microprocessor circuit, which has stored therein a table of reference voltage versus temperature of said sensing portion for detecting a temperature of said sensing portion, determining a reference voltage by retrieving said table on the basis of said detected temperature, obtaining a voltage deviation between said output voltage of said sensing portion and said reference voltage, comparing said voltage deviation with a target air-fuel ratio preset for an air-fuel ratio control of the fuel mixture to generate a control deviation, and producing a fuel control signal in accordance with said control deviation.

12. An air-fuel ratio control apparatus according to claim 10 or 11, wherein said microprocessor circuit in performing said determining function discriminates which is larger between said stoichiometric air-fuel ratio and said preset target air-fuel ratio, and sets a different reference voltage in response to the result of said discrimination.

* * * * *